US009642567B2

(12) United States Patent
Tateda et al.

(10) Patent No.: US 9,642,567 B2
(45) Date of Patent: May 9, 2017

(54) BIOLOGICAL INFORMATION MEASUREMENT DEVICE AND PULSE OXIMETER

(71) Applicant: KONICA MINOLTA, INC., Chiyoda-ku (JP)

(72) Inventors: Norihiro Tateda, Sakai (JP); Masaharu Kanazawa, Suita (JP); Hitoshi Kamezawa, Kyoto (JP)

(73) Assignee: Konica Minolta, Inc., Tokyo (JP)

( * ) Notice: Subject to any disclaimer, the term of this patent is extended or adjusted under 35 U.S.C. 154(b) by 171 days.

(21) Appl. No.: 14/420,299

(22) PCT Filed: Jul. 11, 2013

(86) PCT No.: PCT/JP2013/068951
§ 371 (c)(1),
(2) Date: Feb. 6, 2015

(87) PCT Pub. No.: WO2014/024626
PCT Pub. Date: Feb. 13, 2014

(65) Prior Publication Data
US 2015/0201875 A1 Jul. 23, 2015

(30) Foreign Application Priority Data

Aug. 9, 2012 (JP) ................................. 2012-176954

(51) Int. Cl.
A61B 5/1455 (2006.01)
A61B 5/00 (2006.01)
(Continued)

(52) U.S. Cl.
CPC ........ *A61B 5/14552* (2013.01); *A61B 5/0205* (2013.01); *A61B 5/6826* (2013.01);
(Continued)

(58) Field of Classification Search
CPC .............. A61B 5/1455; A61B 5/14551; A61B 5/14552; A61B 5/6826; A61B 5/6838; A61B 5/684; A61B 5/72
See application file for complete search history.

(56) References Cited

U.S. PATENT DOCUMENTS 6,006,120 A 12/1999 Levin
6,850,788 B2 * 2/2005 Al-Ali ................ A61B 5/14552
600/323
(Continued)

FOREIGN PATENT DOCUMENTS

CN 101015455 8/2007
CN 101080192 11/2007
(Continued)

OTHER PUBLICATIONS

Office Action dated Nov. 8, 2016 which issued in the corresponding Japanese Patent Application No. 2014-529396.

*Primary Examiner* — Eric Winakur
(74) *Attorney, Agent, or Firm* — Cozen O'Connor

(57) ABSTRACT

A device includes a body part and a wearable part integrally attached to the body part and to be worn on a finger, and includes a light source unit and a light receiving unit that are arranged so as to oppose each other. The body part includes an electric circuit including a signal processor, a power supply unit, and a first terminal unit electrically connected to the electric circuit, and the wearable part includes at least one of the light source unit and the light receiving unit, and a second terminal unit electrically connected to the at least one of them. The first and second terminal units are mechanically in contact with and electrically connected to each other. The signal processor acquires a digital value concerning a pulse wave based on a signal output from the light receiving unit receiving light from the light source unit via the finger.

23 Claims, 11 Drawing Sheets

(51) Int. Cl.
  *A61B 5/0205* (2006.01)
  *A61B 5/024* (2006.01)
(52) U.S. Cl.
  CPC .......... *A61B 5/6831* (2013.01); *A61B 5/6838*
      (2013.01); *A61B 5/72* (2013.01); *A61B 5/0004*
          (2013.01); *A61B 5/02427* (2013.01); *A61B*
              *2560/0214* (2013.01); *A61B 2560/0431*
          (2013.01); *A61B 2560/0443* (2013.01); *A61B*
              *2562/0238* (2013.01); *A61B 2562/164*
          (2013.01); *A61B 2562/166* (2013.01); *A61B*
                          *2562/227* (2013.01)

(56) References Cited

U.S. PATENT DOCUMENTS

| | | | |
|---|---|---|---|
| 8,060,171 B2 * | 11/2011 | Hoarau | .............. A61B 5/14552 600/323 |
| 2003/0045784 A1 | 3/2003 | Palatnik et al. | |
| 2010/0240972 A1 | 9/2010 | Neal | |
| 2011/0071370 A1 | 3/2011 | Al-Ali | |

FOREIGN PATENT DOCUMENTS

| | | |
|---|---|---|
| CN | 202015175 U | 10/2011 |
| EP | 1830695 | 12/2005 |
| EP | 2 201 891 | 6/2010 |
| JP | 2004-159810 | 6/2004 |
| JP | 2004-198160 | 7/2004 |
| JP | 2005-110816 | 4/2005 |
| JP | 3142046 | 6/2008 |
| JP | 2011-206286 | 10/2011 |
| WO | WO 03/020129 | 3/2003 |
| WO | WO 2009/113624 | 9/2009 |

\* cited by examiner

BIOLOGICAL INFORMATION MEASUREMENT DEVICE AND PULSE OXIMETER

RELATED APPLICATIONS

This is a U.S. National Phase Application under 35 USC 371 of International Application PCT/JP2013/068951 filed on Jul. 11, 2013.

This application claims the priority of Japanese application no. 2012-176954 filed Aug. 9, 2012, the entire content of which is hereby incorporated by reference.

TECHNICAL FIELD

The present invention relates to biological information measurement devices and pulse oximeters.

BACKGROUND ART

A pulse oximeter that is capable of measuring oxygen saturation of blood ($SpO_2$) is known. In this pulse oximeter, a measurement part that is worn on a part of a body of a subject shines light onto the part of the body, and $SpO_2$ is derived based on the amount of light that passes through or is reflected off the part of the body.

As for this pulse oximeter, a device in which a light source, a sensor, a processor, an amplifier, and the like are arranged in an integrated housing has been proposed (e.g., European Patent No. 1830695). This configuration reduces the manufacturing cost for the device, and makes the device less prone to breakage. Another device that includes a body part to be worn on a wrist and a probe to be fixed on a finger with a strip-shaped tape has been proposed (e.g., Japanese Patent Application Laid-Open No. 2005-110816).

SUMMARY OF THE INVENTION

Problems to be Solved by the Invention

With the technology disclosed in European Patent No. 1830695 above, a special mold is required to integrally mold a housing, and positioning of a circuit board and the like is difficult. In addition, since dimensions of a part of the housing that is worn on a finger (referred to as a wearable part) are determined by dimensions of the special mold, it is difficult to change only the dimensions of the wearable part, for example, to dimensions for adults or dimensions for children. It is therefore necessary to prepare special molds for respective dimensions to manufacture pulse oximeters, but management of inventory and distribution of products is not easy.

With the technology disclosed in Japanese Patent Application Laid-Open No. 2005-110816 above, due to the presence of a body part worn on a wrist and a cable extending from the body part to a probe fixed on a finger, wearing a device for a long time is a heavy burden for subjects.

Such problems commonly occur in devices that are worn on a finger to measure biological information other than oxygen saturation.

The present invention has been conceived in view of the above-mentioned problems, and aims to provide a biological information measurement device and a pulse oximeter that facilitate change of dimensions in manufacturing, and can reduce a burden imposed on subjects by long-time wearing on a finger.

Means for Solving the Problems

In order to solve the above-mentioned problems, a biological information measurement device according to one aspect includes a body part and a wearable part that is integrally attached to the body part and is to be worn on a finger of a living body, and includes a light source unit and a light receiving unit that are arranged so as to oppose each other with the finger therebetween when the wearable part is worn on the finger. The body part includes an electric circuit that includes a signal processing unit, a power supply unit, and a first terminal unit that is electrically connected to the electric circuit. The wearable part includes at least one of the light source unit and the light receiving unit, and a second terminal unit that is electrically connected to the at least one of the light source unit and the light receiving unit. The first terminal unit and the second terminal unit are mechanically in contact with and electrically connected to each other. The signal processing unit acquires a digital value concerning a pulse wave based on a signal output from the light receiving unit by the light receiving unit receiving light that is emitted from the light source unit and passes through the finger.

A pulse oximeter according to another aspect includes a body part and a wearable part that is integrally attached to the body part and is to be worn on a finger of a living body, and includes a light source unit and a light receiving unit that are arranged so as to oppose each other with the finger therebetween when the wearable part is worn on the finger. The body part includes an electric circuit that includes a signal processing unit, a power supply unit, and a first terminal unit that is electrically connected to the electric circuit. The wearable part includes at least one of the light source unit and the light receiving unit, and a second terminal unit that is electrically connected to the at least one of the light source unit and the light receiving unit. The first terminal unit and the second terminal unit are mechanically in contact with and electrically connected to each other. The signal processing unit acquires a value concerning oxygen saturation of blood based on a signal output from the light receiving unit by the light receiving unit receiving light that is emitted from the light source unit and passes through the finger.

Effects of the Invention

The biological information measurement device according to one aspect and the pulse oximeter according to another aspect enable attachment of the wearable part to the body part after the body part and the wearable part are produced separately, and thus dimensions of the wearable part can easily be changed depending on a size of a finger of a subject. As a result, change of dimensions in manufacturing is easy, and a burden imposed on subjects by long-time wearing on the finger can be reduced.

DESCRIPTION OF EMBODIMENT

Figure 1:
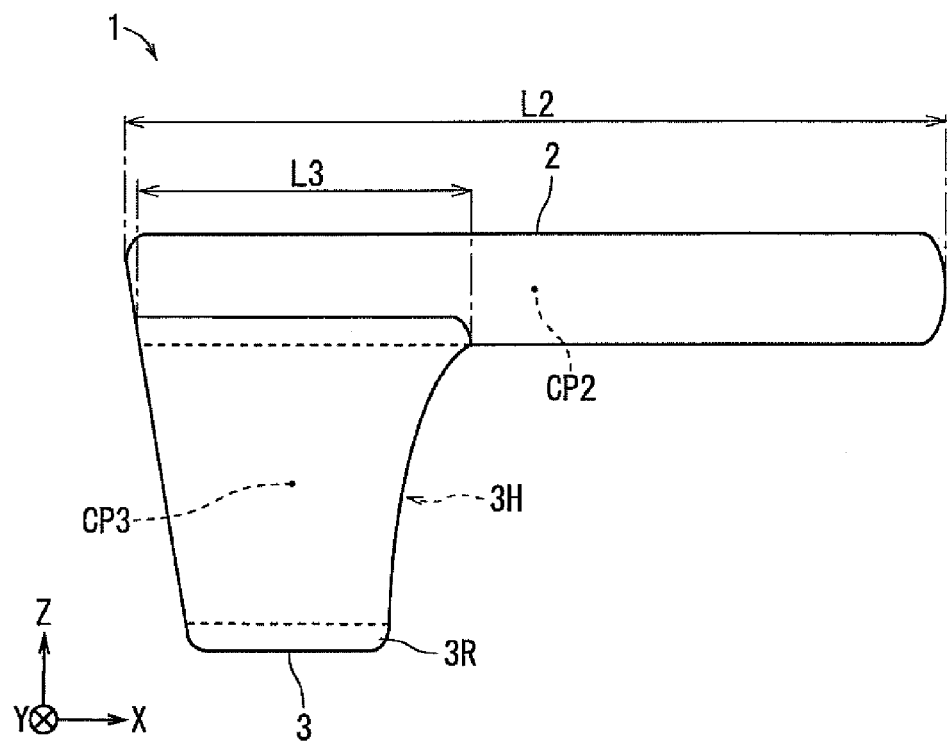
FIG. 1 schematically shows the appearance of a biological information measurement device according to an embodiment.

The following describes an embodiment of the present invention based on the drawings. It should be noted that components having a similar structure and function bear the same reference sign in the drawings, and repetition of description thereof is avoided below. The drawings are those shown schematically, and sizes of and positional relationships among various components in each of the drawings are not accurate. To each of FIGS. 1-7, 10-15, 18, and 21, a right-handed XYZ coordinate system in which one direction along a longitudinal direction of a biological information measurement device 1 (to the right, facing FIG. 1) is defined as a +X direction is assigned.

(1) Embodiment (1-1) Structure of Biological Information Measurement Device

The biological information measurement device 1 according to the embodiment is, for example, a pulse oximeter that acquires a digital value concerning oxygen saturation of blood (an $SpO_2$ value) based on a signal output from a light receiving unit 5 by the light receiving unit 5 receiving light that is emitted from a light source unit 4 and passes through a finger.

Figure 2:
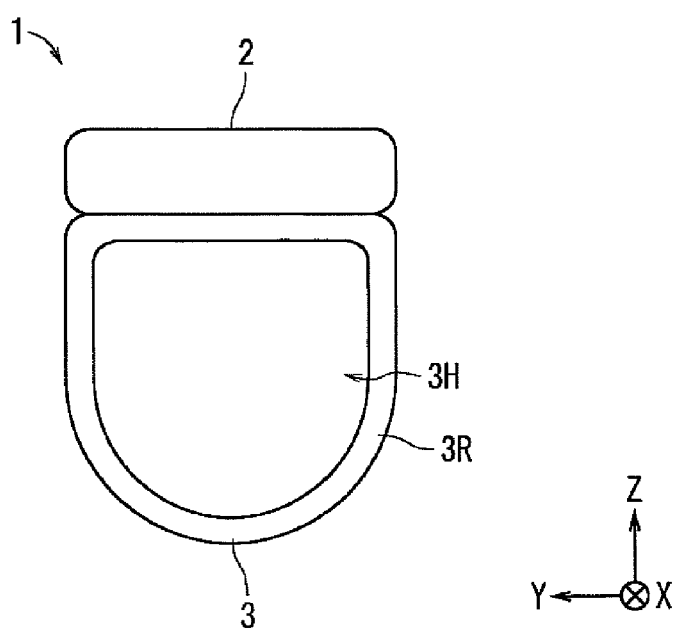
FIG. 2 schematically shows the appearance of the biological information measurement device according to the embodiment.
Figure 3:
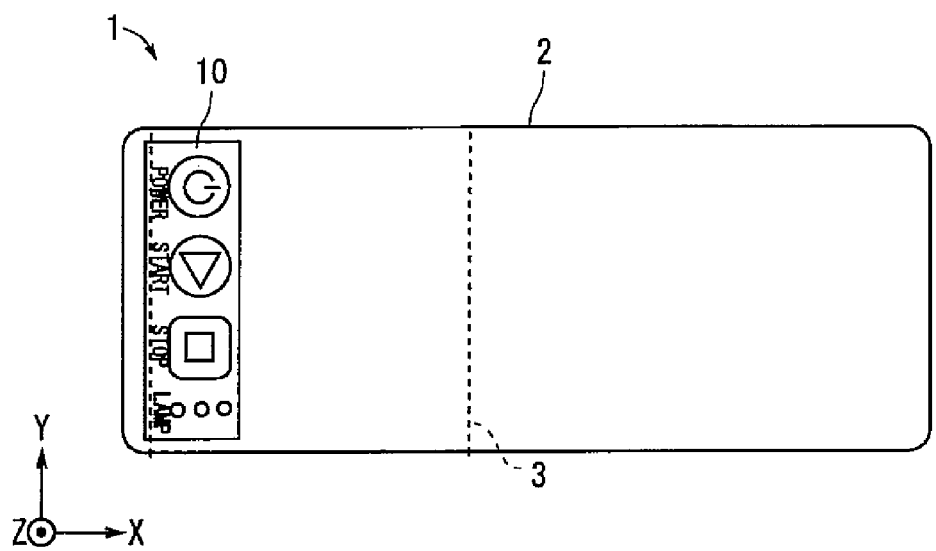
FIG. 3 schematically shows the appearance of the biological information measurement device according to the embodiment.
Figure 4:
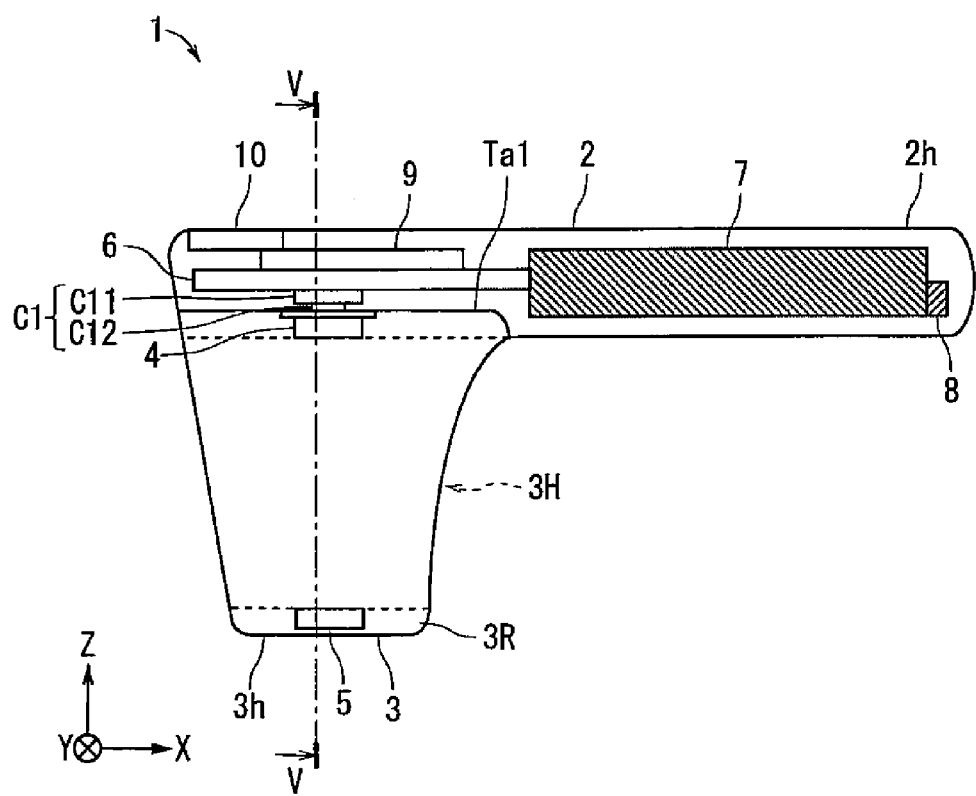
FIG. 4 schematically shows the structure of the biological information measurement device according to the embodiment.
Figure 5:
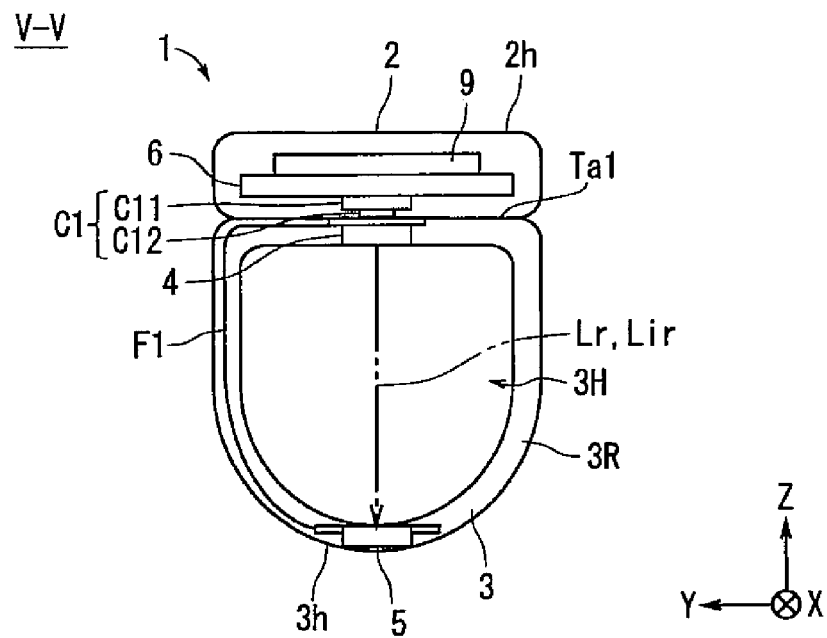
FIG. 5 shows a YZ cross section taken along an alternate long and short dash line V-V of FIG. 4.

FIGS. 1-3 schematically show the appearance of the biological information measurement device 1. FIGS. 1, 2, and 3 are respectively a side view, a front view, and a top view of the biological information measurement device 1. FIGS. 4 and 5 schematically show the structure of the biological information measurement device 1. FIG. 5 shows a YZ cross section taken along an alternate long and short dash line V-V of FIG. 4.

As illustrated in FIGS. 1-5, the biological information measurement device 1 includes a body part 2 and a wearable part 3. The biological information measurement device 1 includes the light source unit 4 and the light receiving unit 5. The light source unit 4 and the light receiving unit 5 are arranged so as to oppose each other with a finger therebetween when the wearable part. 3 is worn on the finger.

The body part 2 includes a housing part 2h, which is a first housing part, as well as various components that are arranged in the housing part 2h. The various components arranged in the housing part 2h include an electric circuit 6, a power supply unit 7, a charging circuit 8, a communication unit 9, an operation unit 10, and a first terminal unit C11. The housing part 2h is approximately in a shape of a cuboid, for example. The housing part 2h is harder than the wearable part 3 and has sufficient rigidity to make the various components stored in the body part 2 less prone to breakage. The first terminal unit C11 is electrically connected to the electric circuit 6.

The wearable part 3 is integrally attached to the body part 2 and is to be worn on a finger of a living body when a variety of information on the living body is measured. When the wearable part 3 is softer than the housing part 2h, the biological information measurement device 1 can provide a comfortable fit for subjects. The wearable part 3 includes the light source unit 4, the light receiving unit 5, and a second terminal unit C12 that is electrically connected to the light source unit 4 and the light receiving unit 5. The second terminal unit C12 is mechanically in contact with and electrically connected to the first terminal unit C11. As a result, the first terminal unit C11 and the second terminal unit C12 form a connection unit C1.

Figure 6:
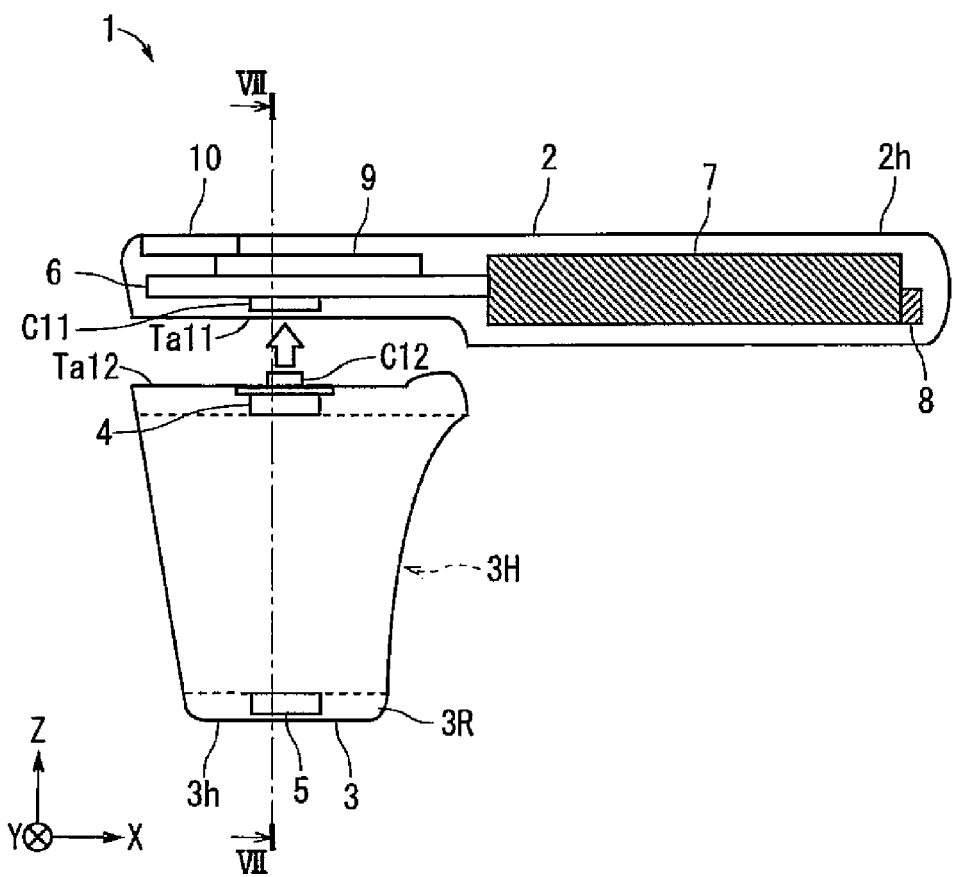
FIG. 6 illustrates a body part and a wearable part before attachment of the wearable part to the body part.
Figure 7:
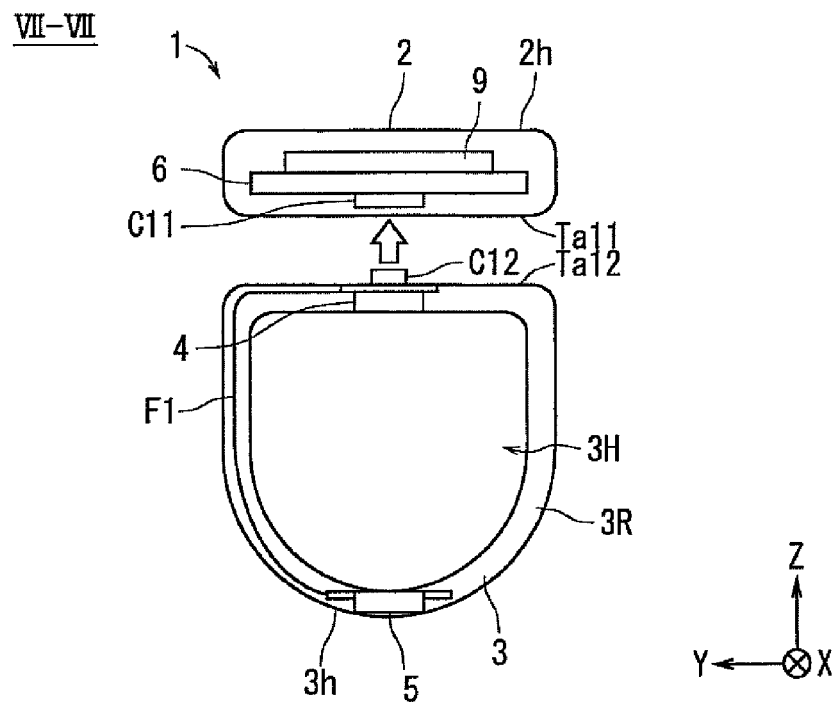
FIG. 7 shows a YZ cross section taken along an alternate long and short dash line VII-VII of FIG. 6.

FIGS. 6 and 7 illustrate the biological information measurement device 1 before attachment of the wearable part 3 to the body part 2. FIG. 7 shows a YZ cross section taken along an alternate long and short dash line of FIG. 6. As illustrated in FIGS. 6 and 7, the wearable part 3 is attached to the body part 2 in a direction that intersects with a longitudinal direction of the body part 2, for example. FIGS. 6 and 7 illustrate an example in which the wearable part 3 is attached to the body part 2 in a +Z direction indicated by an arrow. The body part 2 herein includes the housing part 2h that constitutes a periphery of the body part 2, and the housing part 2h exposes only the first terminal unit C11 to the outside. This configuration ensures waterproofness and other properties of the body part 2, and, for example, makes the body part 2 washable. The wearable part 3 includes a housing part 3h, which is second housing part, that constitutes a periphery of the wearable part 3, and the housing part 3h exposes only the second terminal unit C12 to the outside. This configuration ensures waterproofness and other properties of the wearable part 3, and, for example, makes the wearable part 3 washable.

It is sufficient that the first terminal unit. C11 and the second terminal unit C12 each includes a connecter or an electrode section, for example. When the first terminal unit C11 and the second terminal unit C12 are connecters, and one of the connecters is coupled to the other one of the connecters through fitting, for example, the wearable part 3 can easily be attached to the body part 2 by the connecters.

When the wearable part 3 is detachably attached to the body part 2, the number of wearable parts 3 may be different from the number of body parts 2, and a plurality of wearable parts 3 having different dimensions can sequentially be attached to the body part 2, for example. As a result, the body part 2 can effectively be used.

When a boundary part Ta1 where the body part 2 and the wearable part 3 come into contact with or approach each other in a part other than the connection unit C1 is an adhesion part where the body part 2 and the wearable part 3 adhere to each other with an adhesive agent and the like, the wearable part 3 is less likely to be detached from the body part 2. In this case, a part (also referred to as a coupled part) Ta11 of the body part 2, on a −Z side thereof, to which the wearable part 3 is coupled is different from the first terminal unit C11, and a part (also referred to as a coupling part) Ta12 of the wearable part 3, on the +Z side thereof, that is coupled to the body part 2 is different from the second terminal unit C12. By coupling the coupling part Ta12 to the coupled part Ta11, the wearable part 3 is attached to the body part 2. The coupled part Ta11 and the coupling part. Ta12 may be coupled together by a coupling member, such as a rivet and a screw, for example. That is to say, when the wearable part 3 is attached to the body part 2 by at least one of the adhesion part and the coupling member, the wearable part 3 is less likely to be detached from the body part 2.

Coupling of the coupling part Ta12 to the coupled part Ta11 is not limited to indirect coupling via the adhesion part and the coupling member. For example, the wearable part 3 may be attached to the body part 2 by directly coupling the coupling part. Ta12 to the coupled part Ta11 through various forms, such as fitting, screwing, and engagement. By such forms, a structure to attach the wearable part 3 to the body part 2 can easily be prepared.

When the wearable part 3 includes an elastic body that has elasticity to hold a finger, for example, the biological information measurement device 1 can easily be worn on a finger. Examples of the elastic body are a spring and a polymeric material such as rubber. Specifically, almost the entirety of the wearable part 3 may be made of resin, such as rubber, that has elasticity, and an approximately U-shaped leaf spring may be embedded in resin.

As for a relation between the body part 2 and the wearable part 3 concerning arrangement and dimensions thereof, it is sufficient that a length (also referred to as a first length) L2 of the body part 2 in an X direction, which is a longitudinal direction of the body part 2, is greater than a length (also referred to as a second length) L3 of the wearable part 3 in the X direction. A configuration in which the first length L2 is at least twice the second length L3 is considered as a specific example. Furthermore, it is sufficient that the center position CP3 of the wearable part 3 in the X direction is offset, from the center position CP2 of the body part 2 in the X direction, in one direction (−X direction) toward one end portion (one end portion in a −X direction) of the body part 2 in the longitudinal direction. When such a relation between the body part 2 and the wearable part 3 concerning arrangement and dimensions thereof is satisfied, even in a state in which the biological information measurement device 1 is worn on a finger, movement to bend the finger at its joint is less likely to be interfered with as the wearable part 3 is small, and the body part 2 is less likely to protrude toward a fingertip. As a result, a burden imposed on subjects by long-time wearing of the device on the finger can be reduced.

When the wearable part 3 herein includes a ring part 3R that has an insertion hole 3H into which a finger of a living body is inserted in the −X direction, for example, the insertion hole 3H serves as an area in which the finger is placed when the wearable part 3 is worn on the finger. In this case, the biological information measurement device 1 is worn on a finger quite easily by insertion of the finger into the insertion hole 3H. Furthermore, a burden imposed on the finger inserted into the insertion hole 3H is small, and thus a burden imposed on subjects by long-time wearing of the biological information measurement device 1 on the finger can further be reduced. When the ring part 3R is deformed by elasticity of the elastic body included in the wearable part 3 in a direction in which the insertion hole 3H closes, the biological information measurement device 1 can be stably worn on the finger.

(1-2) Functional Structure of Biological Information Measurement Device

Figure 8:
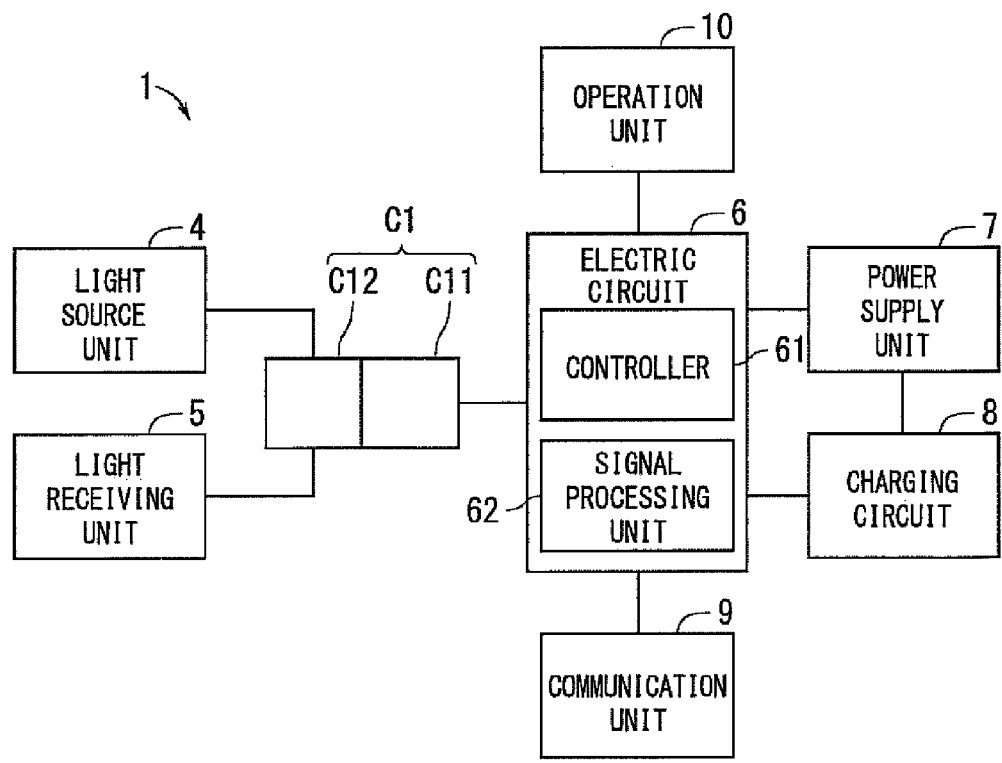
FIG. 8 is a block diagram showing a functional structure of the biological information measurement device according to the embodiment.
Figure 9:
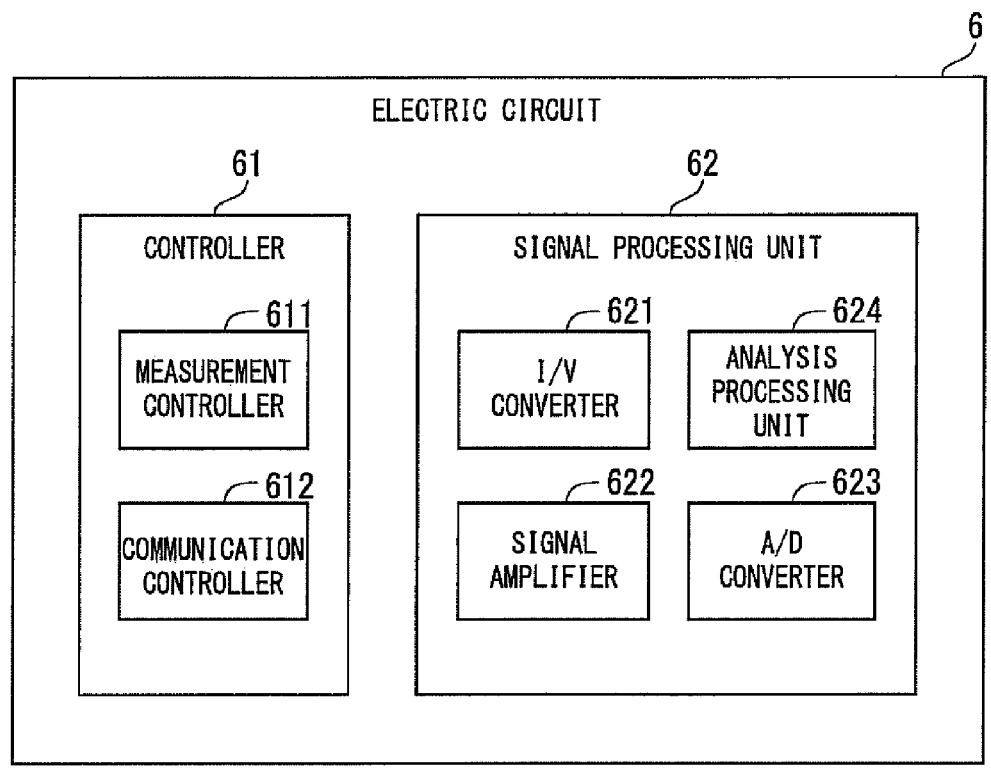
FIG. 9 is a block diagram showing a functional structure of an electric circuit according to the embodiment.

FIGS. 8 and 9 are block diagrams showing the functional structure of the biological information measurement device 1.

As shown in FIG. 8, the biological information measurement device 1 includes the light source unit 4, the light receiving unit 5, the electric circuit 6, the power supply unit 7, the charging circuit 8, the communication unit 9, and the operation unit 10.

The light source unit 4 is electrically connected to the second terminal unit C12. The second terminal unit C12 is electrically connected to the first terminal unit C11, and the first terminal unit C11 is electrically connected to the electric circuit 6. As a result, the light source unit 4 is electrically connected to the electric circuit 6. The light source unit 4 emits light to the light receiving unit 5 by power supply from the power supply unit 7 in accordance with control performed by the electric circuit 6. In FIG. 5, a path along which the light travels (a light path) is indicated by an alternate long and two short dashes line. The light source unit 4 includes a part that emits light at a wavelength $\lambda 1$ of red light and a part that emits light at a wavelength $\lambda 2$ of infrared light. An example of the light source unit 4 is a light emitting diode (LED) or the like. The light source unit 4 alternately emits red light Lr at the wavelength $\lambda 1$ and infrared light Lir at the wavelength $\lambda 2$ during measurement.

The light receiving unit 5 is electrically connected to the second terminal unit C12. As a result, the light receiving unit 5 is electrically connected to the electric circuit 6. The light receiving unit 5 outputs a current signal having a magnitude determined by intensity of received light to a signal processing unit 62, which is described later. The light receiving unit 5 includes a photoelectric conversion element, such as a silicon photodiode, that is at least sensitive to light at the wavelength λ1 and light at the wavelength λ2, for example. In a state in which a finger is inserted into the insertion hole 3H, the light receiving unit 5 receives, from among light at the wavelength λ1 and light at the wavelength λ2 that are emitted from the light source unit 4, light that passes through biological tissues of the finger.

During measurement of biological information, the light source unit 4 alternately emits the red light Lr at the wavelength λ1 and the infrared light Lir at the wavelength λ2, and the light receiving unit 5 performs a light receiving operation in synchronization with the light emitting operation performed by the light source unit 4. The light emitting operation performed by the light source unit 4 and the light receiving operation performed by the light receiving unit 5 can be controlled by a controller 61, which is described later. An operation of projecting and receiving each of the light Lr and the light Lir is repeated in a cycle of approximately 1/100 seconds or more and 1/30 seconds or less, for example.

When the light source unit 4 and the light receiving unit 5 are herein implemented in a flexible printed circuit (FPC: Flexible Printed Circuits) F1, the light source unit 4 and the light receiving unit 5 can easily be incorporated into the biological information measurement device 1. When the light source unit 4 is provided in the body part 2, a wiring path for supplying power to the light source unit 4 can be reduced. As a result, the effects of noise caused on the electric circuit 6 and other units by power supply to the light source unit 4 can be reduced.

The electric circuit 6 includes the controller 61 and the signal processing unit 62. It is sufficient that the electric circuit 6 is configured by various electronic components, integrated circuit components, a CPU, and the like. As shown in FIG. 9, the controller 61 includes a measurement controller 611, a communication controller 612, and a charging circuit controller (not shown). The signal processing unit 62 includes a current/voltage converter (hereinafter, referred to as an I/V converter) 621, a signal amplifier 622, an analog/digital converter (hereinafter, referred to as an A/D converter) 623, and an analysis processing unit 624.

The measurement controller 611 controls operations of the light source unit 4 and the light receiving unit 5. The measurement controller 611 herein causes the light source unit 4 to alternately emit the red light Lr at the wavelength λ1 and the infrared light Lir at the wavelength λ2 each in a cycle of 1/100 seconds, for example. The communication controller 612 controls data communication performed by the communication unit 9, which is described later.

The I/V converter 621 converts a current signal periodically output from the light receiving unit 5 into a voltage signal. The voltage signal is a signal concerning an analog pulse wave (also referred to as a pulse wave signal).

The signal amplifier 622 is an amplifier that amplifies the voltage signal output from the I/V converter 621, for example.

The A/D converter 623 converts the analog pulse wave signal output from the signal amplifier 622 into a digital pulse wave signal. As a result, a digital value concerning a pulse wave can be acquired. That is to say, the digital value concerning the pulse wave can be acquired based on the current signal output from the light receiving unit 5 by the light receiving unit 5 receiving light that is emitted from the light source unit 4 and passes through a finger.

The analysis processing unit 624 performs predetermined data analysis based on the digital pulse wave signal output from the A/D converter 623, thereby calculating various values such as a value of the amount of each of the light Lr and the light Lir received by the light receiving unit 5, a value of amplitude of a pulse wave of each of the light Lr and the light Lir, a value of a ratio of the amplitude of the red light Lr to the amplitude of the infrared light Lir, a value of oxygen saturation of blood (an $SpO_2$ value), a value of a pulse rate, a value of a pulse wave interval (cycle).

The measurement controller 611, the communication controller 612, and the analysis processing unit 624 may be configured by a dedicated electronic circuit, or may be achieved by a microprocessor, a digital signal processor (DSP), and the like executing a program. The I/V converter 621, the signal amplifier 622, and the A/V converter 623 can be configured by a dedicated electronic circuit, for example.

The power supply unit 7 includes, for example, a secondary battery, such as a nickel hydrogen battery or a lithium ion battery. The power supply unit 7 supplies power to various components of the biological information measurement device 1, such as the light source unit 4 and the electric circuit 6. This eliminates the need for a mechanism for replacing a primary battery, such as a dry battery, in the body part 2. As a result, the body part 2 can have a simple and durable structure.

The charging circuit 8 is a circuit for charging the secondary battery included in the power supply unit 7. For example, the secondary battery is charged by connecting a charger to a terminal that is electrically connected to the secondary battery. As a result, the secondary battery can be charged with a simple configuration. When the charging circuit 8 charges the secondary battery without contact, i.e., when the charging circuit 8 includes a circuit for charging the second battery without contact, for example, a terminal and the like for connecting the charger and the like are unnecessary. As a result, the secondary battery can be charged with a simpler configuration. As a method for performing charging without contact, a method of making use of electromagnetic induction in a coil and the like can be used.

The communication unit 9 wirelessly transmits data acquired by the signal processing unit 62. With this structure, a component for analyzing and storing a signal and a display unit for displaying measurement results can be omitted. As a result, reduction in size of the device, power saving, and reduction in manufacturing cost can be achieved.

The communication unit 9 may transmit the digital pulse wave signal acquired by the A/D converter 623 included in the signal processing unit 62, i.e., data of a digital value concerning a pulse wave, for example. In this case, it is sufficient that an external device (e.g., a personal computer) that has received data transmitted from the communication unit 9 calculates various values by using a component corresponding to the analysis processing unit 624. As a result, the structure for processing a signal in the biological information measurement device 1 can be simplified. Therefore, reduction in size of the device, power saving, and reduction in manufacturing cost can further be achieved.

Assume herein that the signal processing unit 62 acquires, based on the digital pulse wave signal, a digital value concerning one or more of a value of oxygen saturation of blood (an $SpO_2$ value), a pulse rate, and a pulse wave interval (cycle). In this case, the communication unit 9 can transmit data of the digital value concerning one or more of the value of oxygen saturation of blood (an $SpO_2$ value), the pulse rate, and the pulse wave interval (cycle) acquired by the signal processing unit 62. As a result, an external device that has received the data transmitted from the communication unit 9 can easily acquire useful information without performing any special arithmetic operation. Furthermore, since a display unit for displaying measurement results in the biological information measurement device 1 can be omitted, reduction in size of the device, power saving, and reduction in manufacturing cost can be achieved.

The electric circuit 6 may include a variety of memory for storing data acquired by the signal processing unit 62.

The operation unit 10 includes a power button, a measurement start button, and a measurement termination button, for example. The power button is a button for performing switching between supply and no supply of power from the power supply unit 7 to each component of the biological information measurement device 1. The measurement start button is a button for starting measurement of a value of oxygen saturation of blood (an $SpO_2$ value) and the like. The measurement termination button is a button for terminating measurement of a value of oxygen saturation of blood (an $SpO_2$ value) or the like.

(1-3) Wearing of Biological Information Measurement Device on Finger

Figure 10:
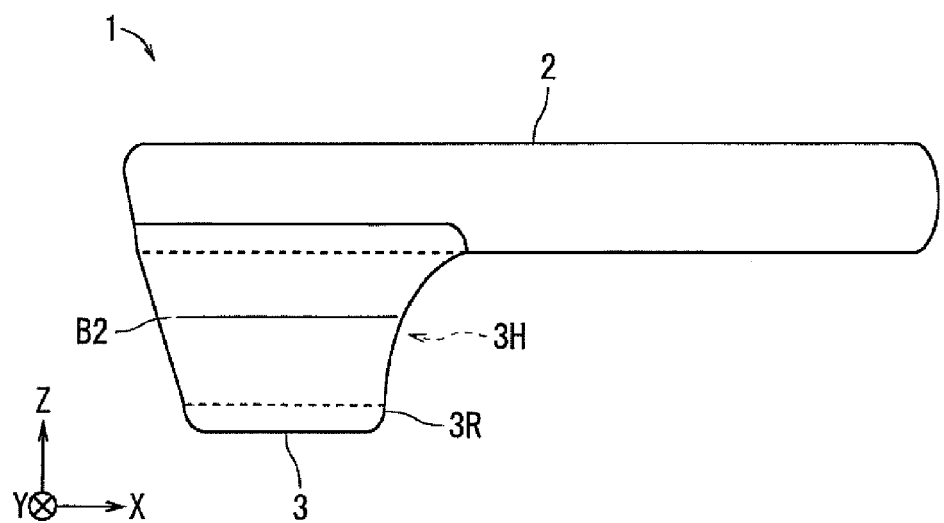
FIG. 10 illustrates how the biological information measurement device according to the embodiment is worn on a finger.
Figure 11:
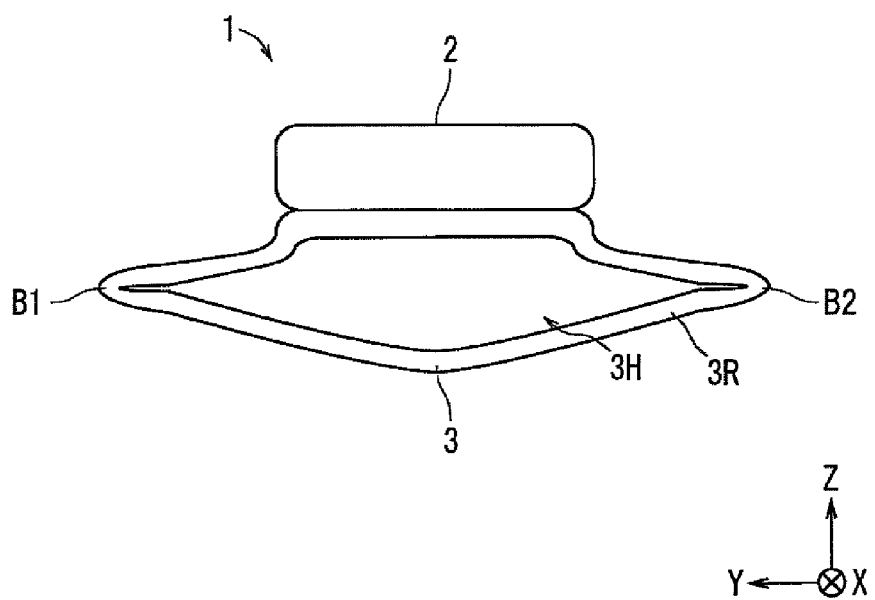
FIG. 11 illustrates how the biological information measurement device according to the embodiment is worn on the finger.
Figure 12:
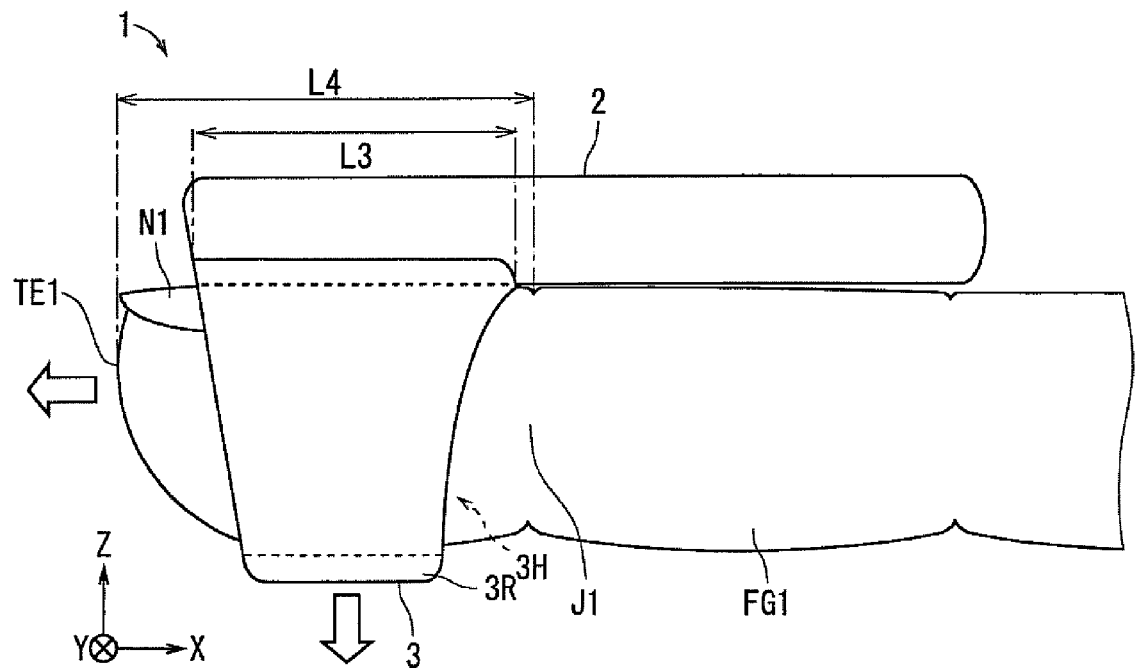
FIG. 12 illustrates how the biological information measurement device according to the embodiment is worn on the finger.

FIGS. 10-12 schematically show one example of how the biological information measurement device 1 is worn on a finger. FIGS. 10 and 11 illustrate one form of the biological information measurement device 1 in a state in which a finger is not inserted into the insertion hole 3H. FIG. 12 illustrates one form of the biological information measurement device 1 in a state in which a finger FG1 is inserted into the insertion hole 3H.

For example, as illustrated in FIGS. 10 and 11, in a state in which the biological information measurement device 1 is not worn on a finger, the elastic body included in the wearable part 3 demonstrates elasticity to hold a finger inserted into the insertion hole 3H, and the ring part 3R is elastically deformed in the Z direction, which is a direction in which the insertion hole 3H closes. In this case, as illustrated in FIG. 11, the ring part 3R can be bent at positions B1 and B2 located on a ±Y side thereof, for example.

When the biological information measurement device 1 is worn on a finger, the ring part 3R is elastically deformed such that the insertion hole 3H is expanded in the −Z direction against elasticity of the elastic body included in the wearable part 3, and, as illustrated in FIG. 12, the finger FG1 is inserted into the insertion hole 3H in the −X direction. As a result, in a state in which the biological information measurement device 1 is worn on the finger FG1, elasticity of the elastic body included in the wearable part 3 attempts to deform the ring part 3R in the Z direction, which is a direction in which the insertion hole 3H closes, and thus the finger FG1 is held by the wearable part 3. In this case, it is sufficient that the finger FG1 is inserted into the insertion hole 3H so that the light source unit 4 shines the light Lr and the light Lir onto an area of the finger FG1 inserted into the insertion hole 3H between a nail N1 and a distal interphalangeal joint (also referred to as a first joint) J1.

As illustrated in FIG. 12, it is sufficient that the second length L3 of the wearable part 3 in the X direction is smaller than a length (also referred to as a third length) L4 from a tip end portion TE1 to the first joint J1 of the finger FG1 in a longitudinal direction of the finger FG1 (herein, the X direction). In this case, when the body part 2 is placed on the nail N1 side (a back side) of the finger FG1, movement to bend the finger FG1 at the first joint J1 is less likely to be interfered with by both of the body part 2 and the wearable part 3. As a result, the biological information measurement device 1 is easily worn on a fingertip, and a burden imposed on subjects by long-time wearing of the biological information measurement device 1 on the fingertip can be reduced.

(1-4) Summary of Embodiment

As described above, in the biological information measurement device 1 according to the embodiment, the wearable part 3 is attached to the body part 2, and the second terminal unit C12 included in the wearable part 3 is mechanically in contact with and electrically connected to the first terminal unit C11 included in the body part 2. With this structure, the wearable part 3 can be attached to the body part 2 after the body part 2 and the wearable part 3 are produced separately. Therefore, dimensions of the wearable part 3 can easily be changed depending on a size of a finger of a subject. Since the wearable part 3 is directly attached to the body part 2, there is no need to wear the body part 2 on a part of a body other than a finger, and a cable and the like for connecting the body part 2 and the wearable part 3 are unnecessary. Thus, dimensions are easily changed in manufacturing of the biological information measurement device 1, and a burden imposed on subjects by long-time wearing of the biological information measurement device 1 on a finger can be reduced.

(2) Modifications

It should be noted that the present invention is in no way limited to the aforementioned embodiment, and can be implemented by making various modifications and improvements without departing from the scope of the present invention.

(2-1) First Modification

Figure 13:
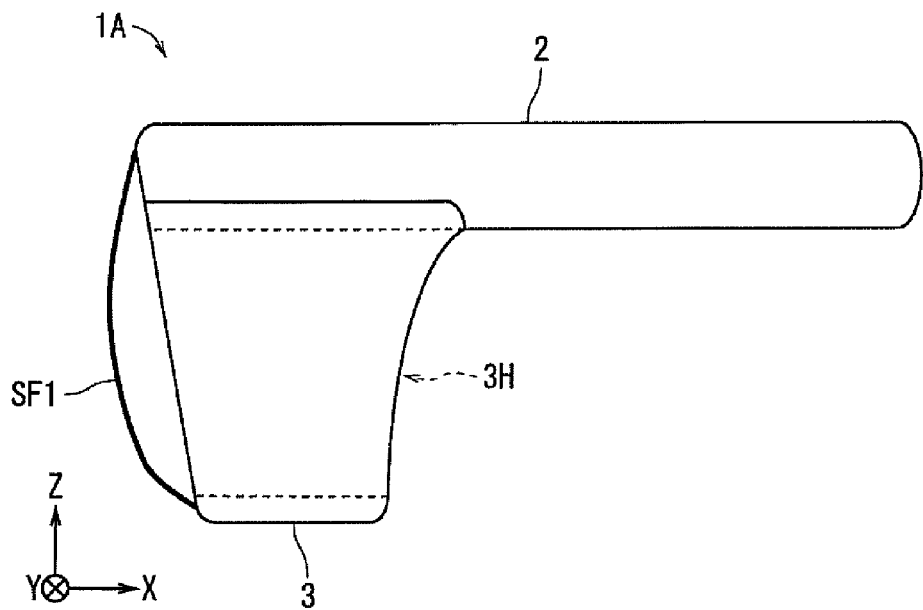
FIG. 13 schematically shows the structure of a biological information measurement device according to a first modification.
Figure 14:
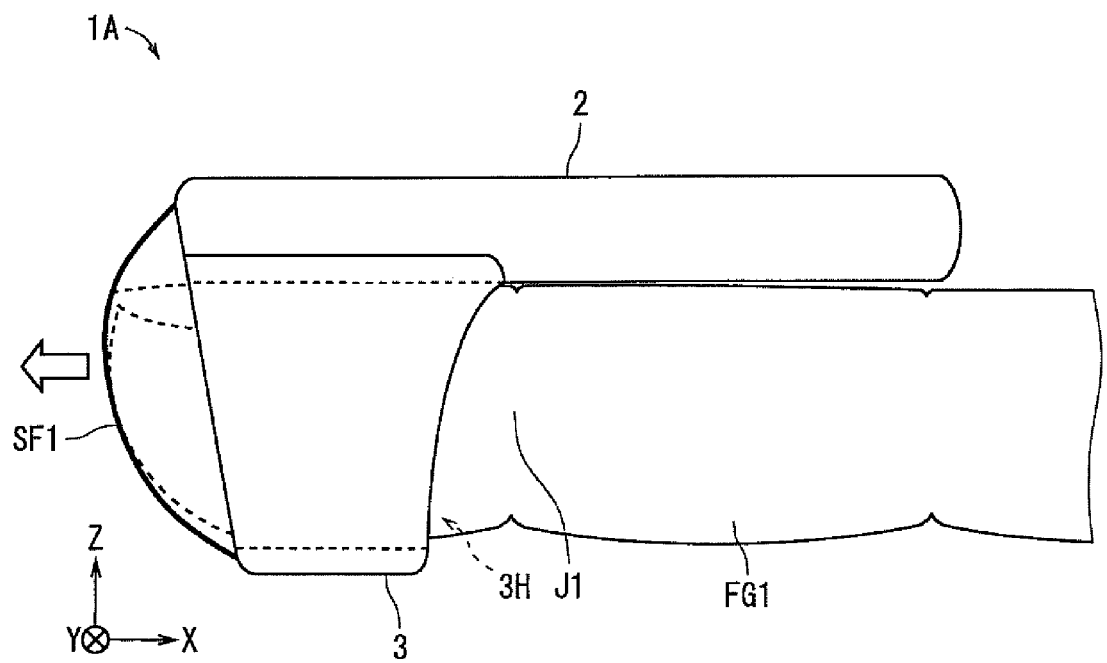
FIG. 14 illustrates how the biological information measurement device according to the first modification is worn on a finger.

Although the insertion hole 3H is a though-hole provided in the ±X direction in the biological information measurement device 1 according to the aforementioned embodiment, the biological information measurement device 1 may not have this structure. For example, as illustrated in FIG. 13, a biological information measurement device 1A that is obtained by adding, to the biological information measurement device 1, a stopper part SF1 at one end portion of the insertion hole 3H of the wearable part 3 in the −X direction may be used. In this case, as illustrated in FIG. 14, by inserting the finger FG1 into the insertion hole 3H from a +X side thereof, and bringing the finger FG1 into contact with the stopper part SF1, the biological information measurement device 1A can be quickly and appropriately worn on the finger FG1 at the position onto which light is to be shined. That is to say, positioning of the biological information measurement device 1A is easy in wearing the biological information measurement device 1A on the finger FG1.

When the stopper part SF1 is a member that has elasticity, such as rubber, the biological information measurement device 1A can easily be worn on a fingertip as the fingertip is less likely to be damaged when the finger FG1 is inserted into the insertion hole 3H. Furthermore, the fingertip easily fits the stopper part SF1, and thus a burden imposed on subjects by long-time wearing of the biological information measurement device 1A on the fingertip can be reduced. When the stopper part SF1 is a light blocking part that blocks passage of light, outside light is less likely to be shined onto the light receiving unit 5 due to the presence of the light blocking part. As a result, measurement errors are less likely to occur.

(2-2) Second Modification

Figure 15:
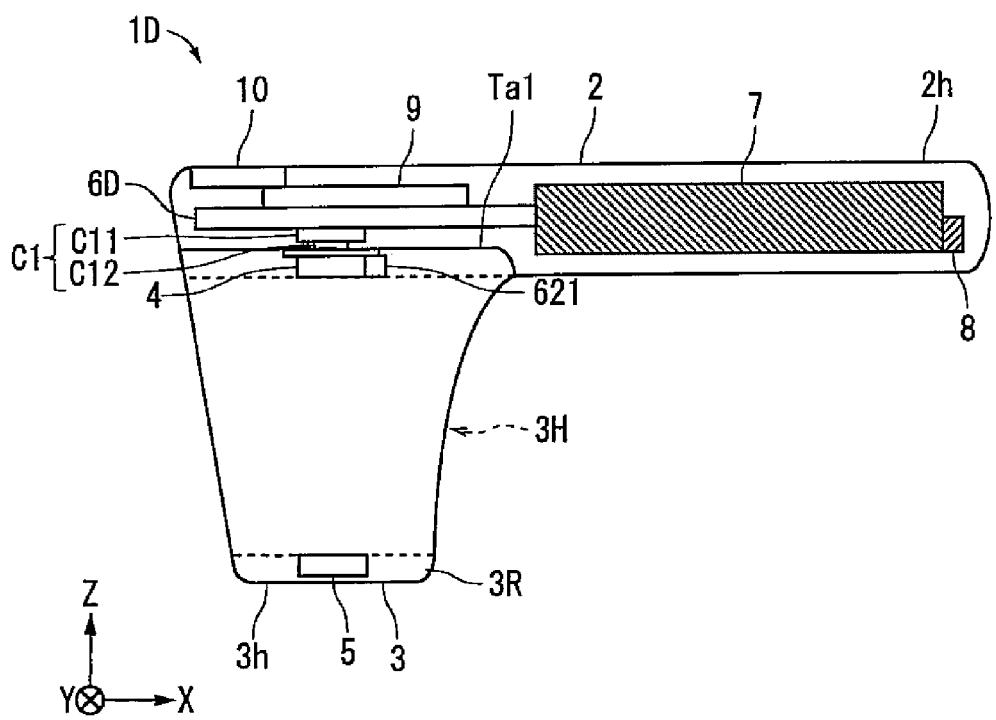
FIG. 15 schematically shows the structure of a biological information measurement device according to a second modification.
Figure 16:
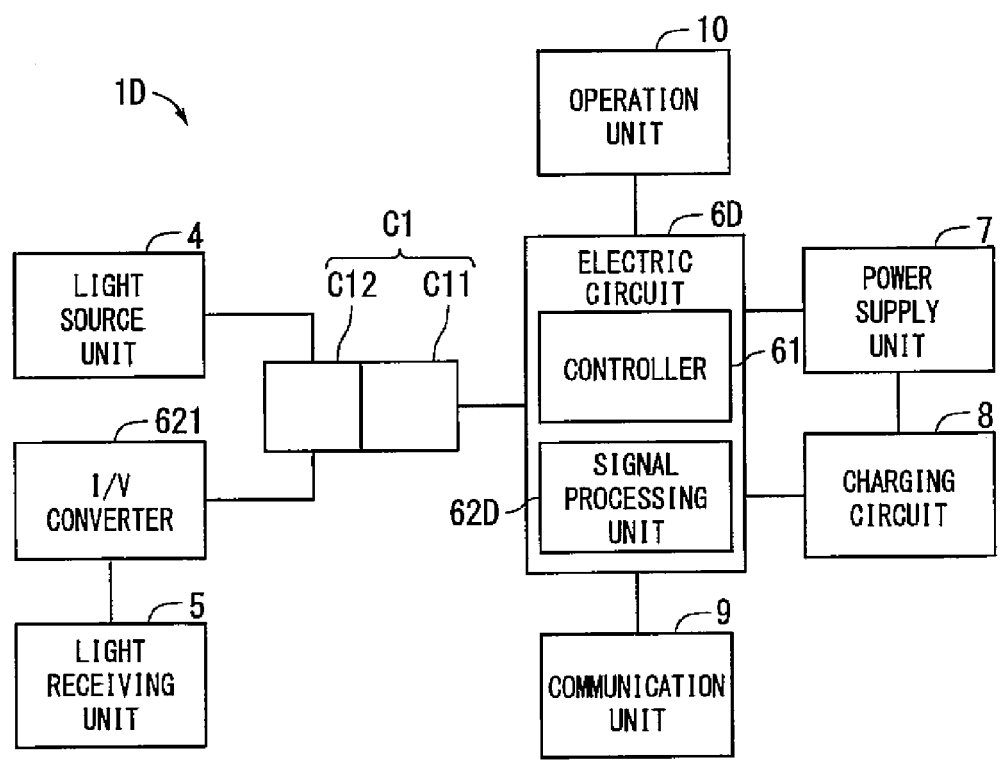
FIG. 16 is a block diagram showing a functional structure of the biological information measurement device according to the second modification.
Figure 17:
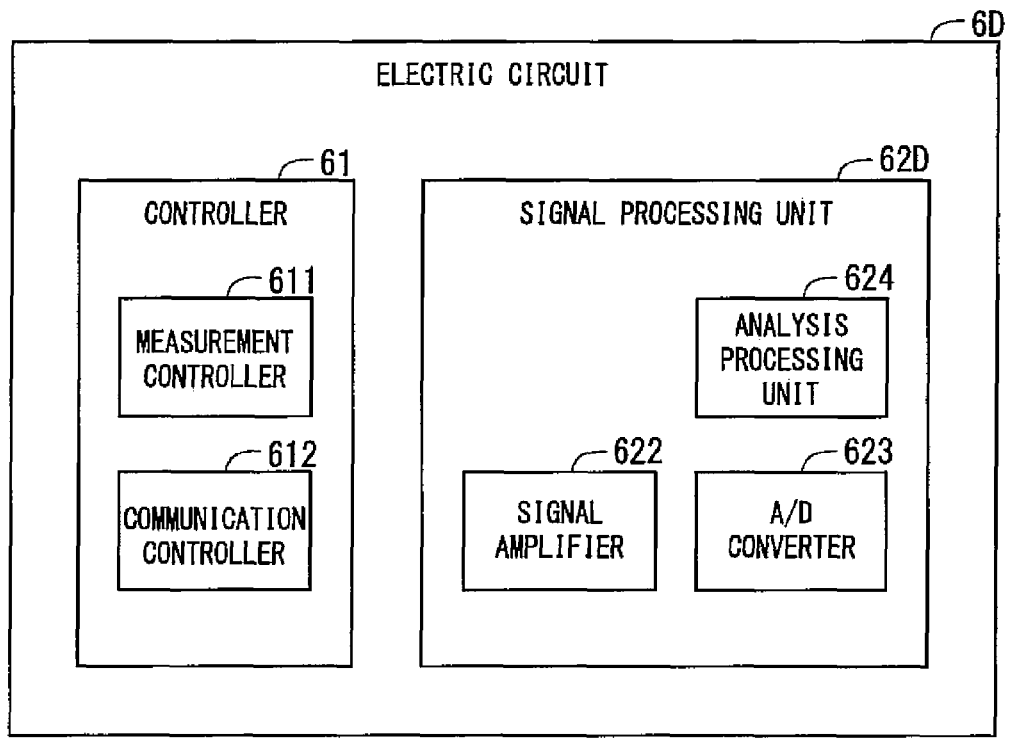
FIG. 17 is a block diagram showing a functional structure of an electric circuit according to the second modification.

Although the electric circuit 6 includes the I/V converter 621 in the biological information measurement device 1 according to the aforementioned embodiment, the biological information measurement device 1 may not have this structure. For example, as shown in FIGS. 15-17, the wearable part 3 may include the light receiving unit 5 and the I/V converter 621 that converts a current signal output from the light receiving unit 5 into an analog voltage signal. In this case, due to reduction of a path along which the current signal is transmitted, the effects of noise can be reduced. Furthermore, a size of the body part 2 can be reduced. A biological information measurement device 1D according to the present modification shown in FIGS. 15-17 is obtained by replacing the electric circuit 6 and the signal processing unit 62 according to the aforementioned embodiment with an electric circuit 6D and a signal processing unit 62D, respectively, with transfer of the I/V converter 621 to the wearable part 3.

(2-3) Third Modification

Figure 18:
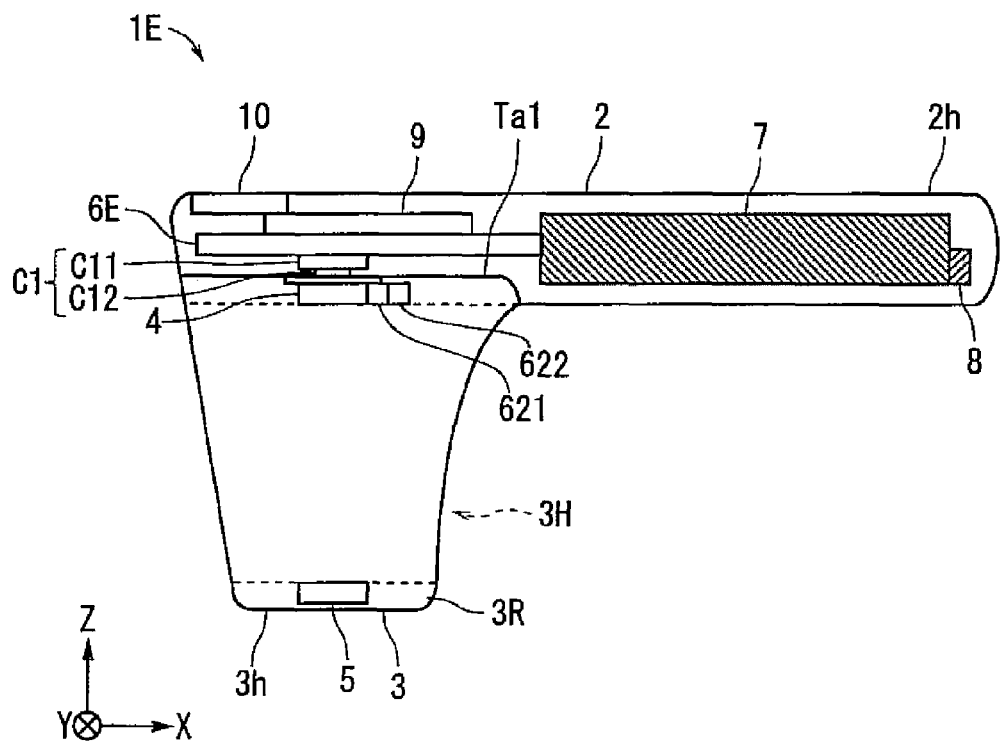
FIG. 18 schematically shows the structure of a biological information measurement device according to a third modification.
Figure 19:
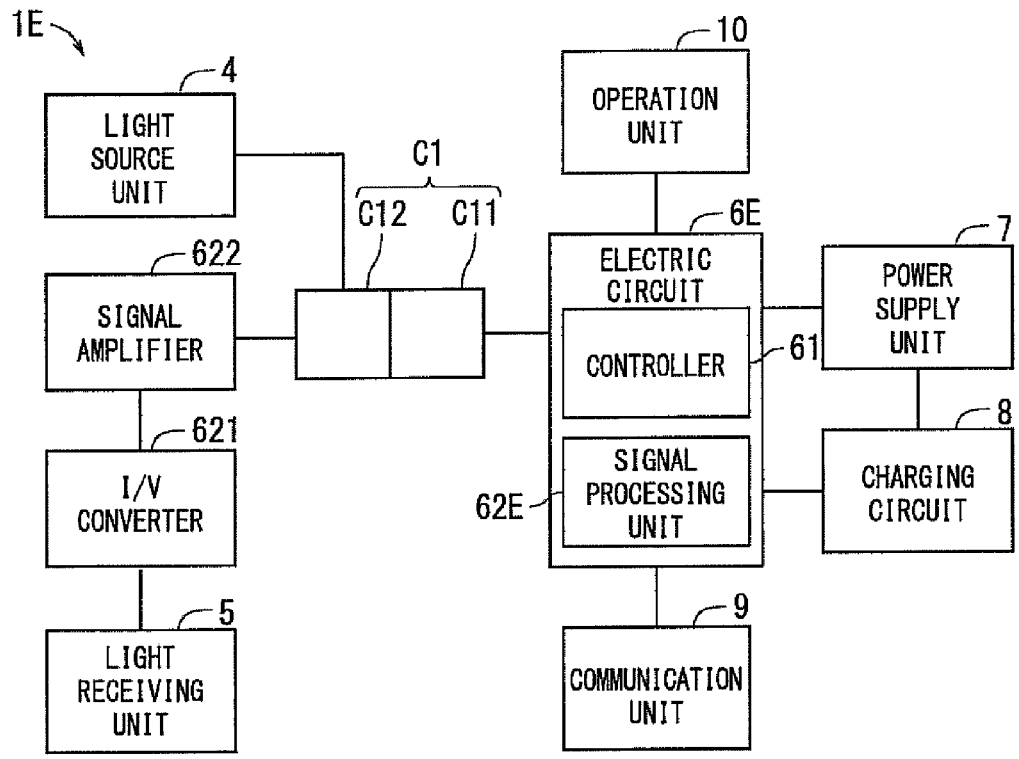
FIG. 19 is a block diagram showing a functional structure of the biological information measurement device according to the third modification.
Figure 20:
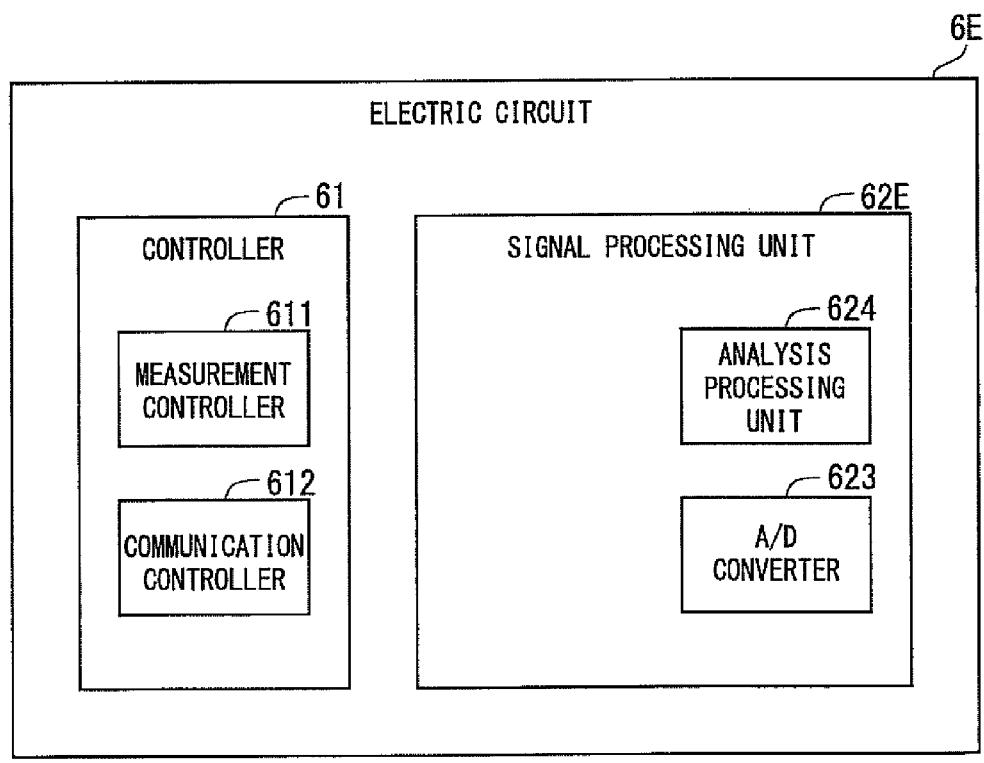
FIG. 20 is a block diagram showing a functional structure of an electric circuit according to the third modification.

Although the electric circuit 6 includes the I/V converter 621 and the signal amplifier 622 in the biological information measurement device 1 according to the aforementioned embodiment, the biological information measurement device 1 may not have this structure. For example, as shown in FIGS. 18-20, the wearable part 3 may include the light receiving unit 5, the I/V converter 621 that converts a current signal output from the light receiving unit 5 into an analog voltage signal, and the signal amplifier 622 that amplifies the voltage signal output from the I/V converter 621. In this case, a size of the body part 2 can further be reduced. A biological information measurement device 1E according to the present modification shown in FIGS. 18-20 is obtained by replacing the electric circuit 6 and the signal processing unit 62 according to the aforementioned embodiment with an electric circuit 6E and a signal processing unit 62E, respectively, with transfer of the I/V converter 621 and the signal amplifier 622 to the wearable part 3.

(2-4) Other Modifications

Figure 21:
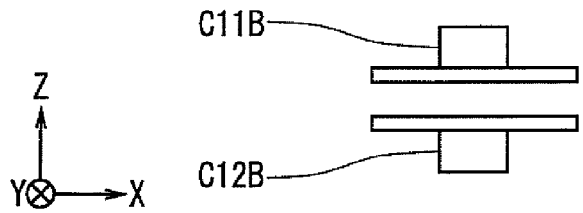
FIG. 21 illustrates a connection unit according to another modification.
Figure 22:
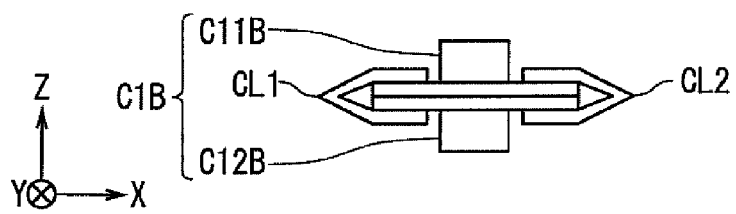
FIG. 22 illustrates the connection unit according to the other modification.
Figure 23:
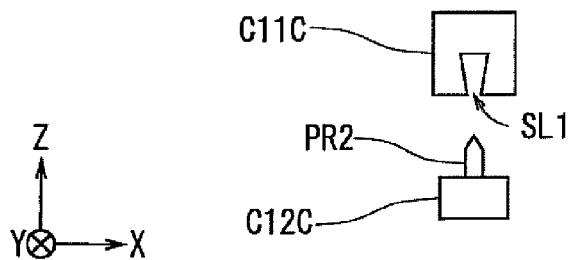
FIG. 23 illustrates a connection unit according to yet another modification.
Figure 24:
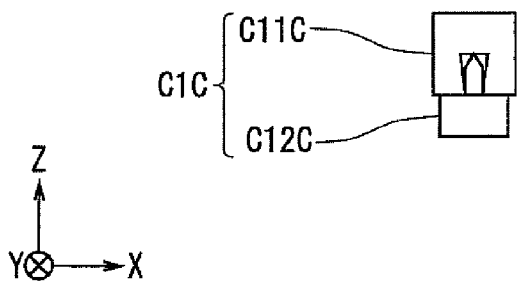
FIG. 24 illustrates the connection unit according to yet the other modification.

Although, as for the biological information measurement device 1 according to the aforementioned embodiment, an example in which the first terminal unit C11 and the second terminal unit C12 are connectors, and the wearable part 3 is attached to the body part 2 through coupling by the connectors is shown, the biological information measurement device 1 may not have this structure. For example, as illustrated in FIGS. 21 and 22, a first terminal unit C11B and a second terminal unit C12B may be brought into contact with each other, and the first terminal unit C11B and the second terminal unit C12B may be held by clips CL1 and CL2, and the like. In this case, the first terminal unit C11B and the second terminal unit C12B held by the clips CL1 and CL2 form a connection unit C1B. Alternatively, as illustrated in FIGS. 23 and 24, a protrusion PR2 of a second terminal unit C12C may be pushed into a recess SL1 in a first terminal unit C11C. In this case, the first terminal unit C1 IC and the second terminal unit C12C form a connection unit C1C.

That is to say, it is sufficient that the wearable part 3 is attached to the body part 2 through at least one of coupling by a connector, holding by a clip, and pushing of one of the parts into the other one of the parts. With this structure, the wearable part 3 is easily attached to the body part 2. Holding by a clip and pushing of one of the parts into the other one of the parts may be used for attachment of the wearable part 3 to the body part 2 in a part other than the first terminal unit C11 and the second terminal unit C12.

Although both of the light source unit 4 and the light receiving unit 5 are provided in the wearable part 3 in the biological information measurement device 1 according to the aforementioned embodiment, the biological information measurement device 1 may not have this structure. For example, at least one of the light source unit 4 and the light receiving unit 5 may be included in the wearable unit 3, and the at least one of the light source unit 4 and the light receiving unit 5 may electrically be connected to the first terminal unit C11. When one of the light source unit 4 and the light receiving unit 5 is provided in the body part 2, cost required for manufacture of the wearable part 3 can be reduced. As a result, change of dimensions in manufacturing, reduction in cost, and power saving are easily achieved. In this case, as for one of the light source unit 4 and the light receiving unit 5 that is provided in the body part 2 rather than in the wearable part 3, it is sufficient that a space and the like that stretches from the insertion hole 3H in the +Z direction is provided in a part of the housing part 3h included in the wearable part 3 so that the housing part 3h does not block the light path. In this case, when the light source unit 4 is provided in the body part 2, a combination of the light source unit 4 and the electric circuit 6 is provided in the body part 2. As a result, the electric circuit 6 can easily perform signal processing in accordance with deviation of wavelength of light emitted from the light source unit 4.

Although both of the light source unit 4 and the light receiving unit 5 are implemented in the flexible printed circuit F1 in the biological information measurement device 1 according to the aforementioned embodiment, the biological information measurement device 1 may not have this structure. For example, when at least one of the light source unit 4 and the light receiving unit 5 is implemented in the flexible printed circuit F1, the light source unit 4 and the light receiving unit 5 can easily be incorporated into the biological information measurement device 1.

Although the first length L2 of the body part 2 in the X direction, which is a longitudinal direction of the body part 2, is greater than the second length L3 of the wearable part 3 in the X direction, which is the longitudinal direction, in the biological information measurement device 1 according to the aforementioned embodiment, the biological information measurement device 1 may not have this structure. For example, the first length L2 and the second length L3 may be approximately equal to each other, and the second length L3 may be greater than the first length L2. In terms of reducing a burden imposed on subjects by long-time wearing of the biological information measurement device 1 on the finger, however, it is preferable that the first length L2 be greater than the second length L3. In this case, movement to bend the finger FG1 at the first joint J1 is less likely to be interfered with by both of the body part 2 and the wearable part 3.

Although the wearable part 3 is attached to a portion near one end portion of the body part 2 in the biological information measurement device 1 according to the aforementioned embodiment, the biological information measurement device 1 may not have this structure. For example, the body part 2 may have a portion that slightly protrudes in the −X direction further than the wearable part 3. That is to say, it is sufficient that the center position CP3 of the wearable part 3 is offset, from the center position CP2 of the body part 2, toward one end portion of the body part 2 in the longitudinal direction. A case where the center position CP3 is not offset, from the center position CP2, toward one end portion of the body part 2 in the longitudinal direction is considered, for example. In terms of reducing a burden imposed on subjects by long-time wearing of the biological information measurement device 1 on the finger, however, it is preferable that the center position CP3 be offset, from the center position CP2, toward one end portion of the body part 2 in the longitudinal direction. In this case, the body part 2 is less likely to protrude toward a fingertip.

Although a display unit is not provided in the biological information measurement device 1 according to the aforementioned embodiment, the biological information measurement device 1 may not have this structure. For example, a display unit for displaying various values acquired by the analysis processing unit 624 may be provided. In this case, the communication controller 612 and the communication unit 9 may be omitted.

Although the wearable part 3 includes the ring part 3R into which the finger FG1 is inserted in the biological information measurement device 1 according to the aforementioned embodiment, the biological information measurement device 1 may not have this structure. For example, the wearable part 3 may have a clip structure that holds the finger FG1. In terms of reducing a burden imposed on subjects by long-time wearing of the biological information measurement device 1 on the finger, however, it is desirable that the wearable part 3 include the ring part 3R into which the finger FG1 is inserted. It is more desirable that the ring part 3R be deformed by elasticity of the wearable part 3 in a direction in which the insertion hole 3H closes.

Although the signal processing unit 62 acquires a digital value concerning oxygen saturation of blood (an $SpO_2$ value) in the biological information measurement device 1 according to the aforementioned embodiment, the biological information measurement device 1 may not have this structure. For example, a biological information measurement device, other than a pulse oximeter, that measures biological information concerning a pulse wave or the like, such as a heart rate, without acquiring the $SpO_2$ value may be used.

It should be appreciated that all or part of the embodiment and various modifications set forth above can appropriately be combined with one another within a reasonable scope.

REFERENCE SIGNS LIST 1, 1A, 1D, 1E Biological information measurement device
2 Body part
2h, 3h Housing
3 Wearable part
3H Insertion hole
3R Ring part
4 Light source unit
5 Light receiving unit
6, 6D, 6E Electric circuit
7 Power supply unit
8 Charging circuit
9 Communication unit
10 Operation unit
61 Controller
62, 62D, 62E Signal processing unit
621 Current/voltage converter (I/V converter)
622 Signal amplifier
623 Analog/digital converter (A/D converter)
624 Analysis processing unit
C1, C1B, C1C Connection unit
C11, C1B, C11C First terminal unit
C12, C12B, C12C Second terminal unit
CL1, CL2 Clip
CP2 Center position
CP3 Center position
F1 Flexible printed circuit
FG1 Finger
SF1 Stopper part
Ta1 Boundary part
Ta11 Coupled part
Ta12 Coupling part

The invention claimed is:

1. A biological information measurement device comprising:
a body part; and
a wearable part that is directly and detachably attached to the body part and is to be worn on a finger of a living body, the wearable part and the body part being in physical contact with each other,
wherein the biological information measurement device includes a light source unit and a light receiving unit that are arranged so as to oppose each other with said finger therebetween when said wearable part is worn on said finger,
wherein said body part includes an electric circuit, a power supply unit, and a first terminal unit, the electric circuit including a signal processing unit, the first terminal unit being electrically connected to the electric circuit,
wherein said wearable part includes at least one of said light source unit and said light receiving unit, and a second terminal unit that is electrically connected to the at least one of said light source unit and said light receiving unit,
wherein said first terminal unit and said second terminal unit are mechanically in contact with and electrically connected to each other,
wherein said signal processing unit acquires a digital value concerning a pulse wave based on a signal output from said light receiving unit, the signal being output by said light receiving unit receiving light that is emitted from said light source unit and passes through said finger, and
wherein said wearable part is selectable in response to a size of said finger among a plurality of wearable parts having different dimensions.

2. The biological information measurement device according to claim 1, wherein said first terminal unit and said second terminal unit each include a connecter or an electrode section.

3. The biological information measurement device according to claim 1,
wherein said body part includes a first housing part that exposes said first terminal unit to the outside, and
wherein said wearable part includes a second housing part that exposes said second terminal unit to the outside.

4. The biological information measurement device according to claim 3, wherein said first housing part is harder than said wearable part.

5. The biological information measurement device according to claim 1, wherein an attachment structure of said wearable part to said body part includes at least one of coupling by a connector, holding by a clip, and pushing of one of the body part and the wearable part into the other one of the body part and the wearable part.

6. The biological information measurement device according to claim 1,
wherein said body part includes a coupled part that is different from said first terminal unit,
wherein said wearable part includes a coupling part that is different from said second terminal unit, and
wherein said wearable part is attached to said body part by coupling said coupling part to said coupled part.

7. The biological information measurement device according to claim 6, wherein said coupling part included in said wearable part is coupled to said coupled part included in said body part by at least one of an adhesion part and a coupling member.

8. The biological information measurement device according to claim 1, wherein at least one of said light source unit and said light receiving unit is implemented in a flexible printed circuit.

9. The biological information measurement device according to claim 1, wherein said wearable part includes said light receiving unit and a converter that converts a current signal output from said light receiving unit into a voltage signal.

10. The biological information measurement device according to claim 9, wherein said wearable part includes a signal amplifier that amplifies said voltage signal output from said converter.

11. The biological information measurement device according to claim 1, wherein said power supply unit includes a secondary battery.

12. The biological information measurement device according to claim 11, wherein said body part further includes a charging circuit that charges said secondary battery.

13. The biological information measurement device according to claim 12, wherein said charging circuit includes a circuit that charges said secondary battery without contact.

14. The biological information measurement device according to claim 1, wherein said body part further includes a communication unit that wirelessly transmits data acquired by said signal processing unit.

15. The biological information measurement device according to claim 14, wherein said communication unit transmits data of the digital value concerning said pulse wave acquired by said signal processing unit.

16. The biological information measurement device according to claim 14,
wherein said signal processing unit acquires, based on the digital value concerning said pulse wave, a digital value concerning one or more of oxygen saturation of blood, a pulse rate, and a pulse wave interval, and
wherein said communication unit transmits data of the digital value concerning one or more of said oxygen saturation of blood, said pulse rate, and said pulse wave interval acquired by said signal processing unit.

17. The biological information measurement device according to claim 1, wherein said wearable part includes an elastic body that has elasticity to hold said finger.

18. The biological information measurement device according to claim 1, wherein said wearable part includes a ring part that has an insertion hole into which said finger is inserted in one direction.

19. The biological information measurement device according to claim 18, wherein said ring part is deformed by elasticity in a direction in which said insertion hole closes.

20. The biological information measurement device according to claim 18, wherein said wearable part includes a stopper part that is provided at one end portion of said insertion hole in said one direction.

21. The biological information measurement device according to claim 20, wherein said stopper part includes a light blocking part.

22. The biological information measurement device according to claim 1,
wherein a first length of said body part in a longitudinal direction of the body part is greater than a second length of said wearable part in the longitudinal direction, and
wherein a center position of said wearable part in said longitudinal direction is offset, from a center position of said body part in said longitudinal direction, in one direction toward one end portion of said body part in said longitudinal direction.

23. A pulse oximeter comprising:
a body part; and
a wearable part that is directly and detachably attached to the body part and is to be worn on a finger of a living body, the wearable part and the body part being in physical contact with each other,
wherein the pulse oximeter includes a light source unit and a light receiving unit that are arranged so as to oppose each other with said finger therebetween when said wearable part is worn on said finger,
wherein said body part includes an electric circuit, a power supply unit, and a first terminal unit, the electric circuit including a signal processing unit, the first terminal unit being electrically connected to the electric circuit,
wherein said wearable part includes at least one of said light source unit and said light receiving unit, and a second terminal unit that is electrically connected to the at least one of said light source unit and said light receiving unit,
wherein said first terminal unit and said second terminal unit are mechanically in contact with and electrically connected to each other,
wherein said signal processing unit acquires a value concerning oxygen saturation of blood based on a signal output from said light receiving unit, the signal being output by said light receiving unit receiving light that is emitted from said light source unit and passes through said finger, and
wherein said wearable part is selectable in response to a size of said finger among a plurality of wearable parts having different dimensions.

\* \* \* \* \*